United States Patent
Moore et al.

(10) Patent No.: US 11,872,295 B2
(45) Date of Patent: Jan. 16, 2024

(54) METHOD AND APPARATUS FOR DYEING HAIR FIBRES USING RADIO FREQUENCY ELECTROMAGNETIC RADIATION

(71) Applicant: Jemella Limited, Leeds (GB)

(72) Inventors: Timothy David Moore, Cambridge (GB); Roger Williamson, Cambridge (GB); Mathias Herrlein, Cambridge (GB); Simon Godfrey, Cambridge (GB); Liam Wright, Cambridge (GB); Matthew James, Cambridge (GB); Hendrik Riedel, Cambridge (GB)

(73) Assignee: Jemella Limited, Leeds (GB)

( * ) Notice: Subject to any disclaimer, the term of this patent is extended or adjusted under 35 U.S.C. 154(b) by 839 days.

(21) Appl. No.: 16/956,427

(22) PCT Filed: Dec. 18, 2018

(86) PCT No.: PCT/GB2018/053662
§ 371 (c)(1),
(2) Date: Jun. 19, 2020

(87) PCT Pub. No.: WO2019/122850
PCT Pub. Date: Jun. 27, 2019

(65) Prior Publication Data
US 2023/0181429 A1 Jun. 15, 2023

(30) Foreign Application Priority Data
Dec. 22, 2017 (GB) ...................................... 1721770

(51) Int. Cl.
*A61Q 5/10* (2006.01)
*A61K 8/04* (2006.01)
(Continued)

(52) U.S. Cl.
CPC .................. *A61K 8/04* (2013.01); *A45D 2/00* (2013.01); *A61Q 5/00* (2013.01); *A61Q 5/10* (2013.01);
(Continued)

(58) Field of Classification Search
CPC .............. A61K 8/04; A61K 2800/4322; A61K 2800/522; A61K 2800/83; A45D 2/00; A45D 2002/003; A61Q 5/08; A61Q 5/10
(Continued)

(56) References Cited

U.S. PATENT DOCUMENTS 6,425,403 B1 * 7/2002 Lin Lu .................. A45D 19/18
132/270

FOREIGN PATENT DOCUMENTS

CN 107088090 A 8/2017
EP 3015135 A1 5/2016
(Continued)

OTHER PUBLICATIONS

"International Application Serial No. PCT/GB2018/053662, International Search Report dated Mar. 19, 2019", (dated Mar. 19, 2019), 4 pgs.
(Continued)

*Primary Examiner* — Eisa B Elhilo
(74) *Attorney, Agent, or Firm* — Merchant & Gould P.C.

(57) ABSTRACT

The present invention relates to a method for dyeing hair fibres, in particular a method which involves coating hair fibres with a hair dye composition and directing radio frequency electromagnetic radiation to the coated hair fibres to cause heating within the coated hair fibres by dielectric loss. The present invention also relates to kits and appliances for use in connection with the method, as well as the use of radio frequency electromagnetic radiation in reducing the effective dye-treatment time for hair fibres. In one aspect,
(Continued)

there is provided a method of dyeing hair fibres, said method comprising the steps of: i) coating one or more hair fibres with a hair dye composition; and ii) directing radio frequency electromagnetic radiation having one or more frequencies from 1 MHz to 300 MHz to the one or more coated hair fibres to cause heating within the one or more coated hair fibres by dielectric loss. Preferably, the hair dye composition used in step i) is a permanent or demi-permanent hair dye composition that may be prepared by combining a dye lotion containing one or more dye precursors and an activator solution containing an activating agent, wherein the activating agent in the activator solution converts the one or more dye precursors in the dye lotion to active dye agents.

20 Claims, 3 Drawing Sheets

(51) Int. Cl.
*A45D 2/00* (2006.01)
*A61Q 5/00* (2006.01)

(52) U.S. Cl.
CPC ............... *A45D 2002/003* (2013.01); *A61K 2800/4322* (2013.01); *A61K 2800/522* (2013.01); *A61K 2800/83* (2013.01)

(58) Field of Classification Search
USPC .......................................................... 8/405
See application file for complete search history.

(56) References Cited

FOREIGN PATENT DOCUMENTS

| WO | WO-2006060567 A2 | 6/2006 |
| WO | WO-2011067707 A2 | 6/2011 |
| WO | WO-2011141882 A1 | 11/2011 |
| WO | WO-2013125054 A1 | 8/2013 |
| WO | WO-2013140371 A1 | 9/2013 |

OTHER PUBLICATIONS

"International Application Serial No. PCT/GB2018/053662, Written Opinion dated Mar. 19, 2019", (dated Mar. 19, 2019), 8 pgs.
"United Kingdom Application Serial No. 1721770.4, Search Report dated Jun. 21, 2018", (dated Jun. 21, 2018), 4 pgs.

* cited by examiner

METHOD AND APPARATUS FOR DYEING HAIR FIBRES USING RADIO FREQUENCY ELECTROMAGNETIC RADIATION

PRIORITY APPLICATIONS

This application is a U.S. National Stage Filing under 35 U.S.C. 371 from International Application No. PCT/GB2018/053662, filed on Dec. 18, 2018, and published as WO2019/122850 on Jun. 27, 2019, which claims the benefit of priority to Great Britain Application No. 1721770.4, filed on Dec. 22, 2017; the benefit of priority of each of which is hereby claimed herein, and which applications and publication are hereby incorporated herein by reference in their entireties.

The present invention relates to a method for dyeing hair fibres, in particular a method which involves coating hair fibres with a hair dye composition and directing radio frequency electromagnetic radiation to the coated hair fibres to cause heating within the coated hair fibres by dielectric loss. The present invention also relates to kits and appliances for use in connection with the method, as well as the use of radio frequency electromagnetic radiation in reducing the effective dye-treatment time for hair fibres.

Hair dyeing has long been used for cosmetic purposes for modifying the colour of hair. Permanent hair dyeing processes typically involve exposing the outer cuticle layer of the hair shaft to alkalizing agents, typically ammonia or monoethanolamine, which cause the hair shaft to swell enabling a developer, for instance an oxidising agent, and/or hair dye agents to penetrate through the cuticle layer into the cortex of the hair shaft. Melanins located in the cortex, which are responsible for hair's natural pigmentation, are subsequently decolourized or solubilized and removed. The developer is also typically employed to convert one or more dye precursors in a hair dye composition to active dye agents which, when deposited in the cortex of the hair shaft, give rise to colouring of the hair fibres.

Conventional approaches to hair dyeing have relied on the application of a hair dye composition to the hair fibres which is then left for a period of time for dyeing to be accomplished. Often, the coated hair fibres are also exposed to heat to activate the dye composition and/or accelerate the dyeing process, usually supplied by means of a hand-held blow-dryer or larger fixed place heating lamps typically used in hair salons. The process of hair dyeing is known to be cumbersome and can be a significant time expense for individuals regularly undergoing hair dyeing.

Another issue that can be a problem with hair dyeing is the heating that often accompanies the process. Typically, temperatures of at least 50° C. are utilized to heat a dye composition once applied, often over an extended period of 30 to 45 minutes, in order to achieve an acceptable colour transition in the hair fibres. However, prolonged overheating of coated hair fibres has been known to cause damage to hair, for instance as a result of "hot-spots" forming in the hair fibres where heat is applied unevenly and detrimentally high temperatures are developed. This can materially change the composition of the hair fibres and can ultimately lead to breakage and loss in severe cases. In addition, prolonged exposure of hair fibres to oxidising agents such as hydrogen peroxide used in permanent hair dye compositions can result in compositional changes to the keratin which can cause loss of tensile properties and damage to the hair.

U.S. Pat. No. 6,425,403 describes a hair dyeing process utilizing heat application devices aimed at accelerating the dyeing process and minimizing hair damage. Heat is applied to the coated hair by means of a hand-held hot-air blow dryer for a period of time, after which a shower cap and/or moistened towel is applied to the head so as to retain heat in the coated hair fibres. However, it would be preferable if the dyeing process could be accelerated, whilst avoiding damage to the hair fibres, without the need for a shower cap and/or towel to be placed on the individual's head.

WO 2009/144557 describes the use of a heating device for reducing the effective hair dyeing time. A hair dye composition is placed in a container of the heating device and heated in a controlled manner to a desired temperature. Once a desired temperature is reached, the heated dye composition is subsequently applied to hair fibres so as to avoid application of heat directly to coated hair fibres in the normal manner using a handheld hot-air blower or heating lamp.

There remains a need for an alternative means for accelerating the hair dyeing process which avoids the problems associated with the application of heat associated with conventional hair dyeing processes.

The present invention is based on the surprising discovery that radio frequency electromagnetic radiation may be effectively employed in accelerating the hair dyeing process whilst avoiding the problems of heat damage associated with conventional heat accelerated dye processes. Furthermore, by reducing the effective dyeing time, the exposure of the hair to potentially damaging hair dye components (for example, oxidizing agents such as hydrogen peroxide) may be reduced and the negative impacts of such components minimized.

In a first aspect, the present invention provides a method of dyeing hair fibres, said method comprising the steps of: i) coating one or more hair fibres with a hair dye composition; and ii) directing radio frequency electromagnetic radiation having one or more frequencies from 1 MHz to 300 MHz to the one or more coated hair fibres to cause heating within the one or more coated hair fibres by dielectric loss.

The present invention takes advantage of dielectric heating, specifically resulting from exposure to radio frequency electromagnetic radiation. Dielectric heating is known to induce heating by dielectric loss following dipole rotation of polar molecules as a result of interaction with a rapidly oscillating electric field. Dielectric heating in commercial applications is most commonly observed where the polar molecule is water. It has been found by the present inventors that radio frequency electromagnetic radiation, and dielectric heating resulting therefrom, can substantially accelerate a hair dyeing process. Surprisingly, this has even been found to be the case where a hair dye composition is used containing substantially no water, indicating that acceleration of the dyeing process is not merely related to heating of the dye composition alone As discussed for instance, in Barba et al., Thermochimica Acta, 494 (2009), pages 136 to 140, hair fibres have both an internal and external water content. Without being bound by any particular theory, it is believed that water naturally associated with hair fibres themselves may give rise to dielectric heating which can in turn accelerate the hair dyeing process. In particular, it is believed that heating of the hair fibres as a result of dielectric losses in water molecules associated therewith may lead to changes in the outer cuticle layer so as to accelerate penetration of components of the hair dye composition into the cortex of the hair fibres.

As a result of the internal water content of hair fibres, dielectric heating of the hair fibre may be considered to occur from the inside of the hair fibre. This is in contrast to conventional heating processes which provide an external source of heat to the hair. As there is also an external water content associated with hair fibres (and heat energy may be transferred from a heated hair fibre to a coating thereon) heating of a dye composition coated on hair fibres, even where the dye composition is non-aqueous, will also occur and therefore may also accelerate the formation of active dye agents.

The natural internal and external water content of hair is generally uniformly distributed over the hair fibre. Consequently, dielectric heating deriving from dielectric losses from water molecules associated with the hair gives rise to uniform heating of the hair fibres themselves. This again contrasts with conventional hair heating processes, where heating provided by an external heat source is not uniform over the entire surface of the majority of hair fibres. Thus, the surprising reduction in the effective hair dyeing time observed for the present invention is believed to derive predominantly from internal heating of the hair fibres as well as the uniformity of heating which is achievable by means of the process.

In accordance with the present invention, in step i) of the method a hair dye composition is coated on to one or more hair fibres. The one or more hair fibres coated in accordance with the present invention are preferably keratinous hair fibres and may therefore be any form of human or animal hair, although the method of the invention is preferably applied to human hair. As will be appreciated, the method of the invention may be applied to one or more hair fibres whilst associated with the human or animal body ("living" hair fibres) or may be applied to one or more extracted hair fibres ("non-living" hair fibres) that are, for instance, intended for a hair piece or wig. The benefits of the invention may also extend to synthetic hair fibres, for example non-keratinous fibres, including fibres of modacrylic (comprising acrylonitriles), vinyl chloride, vinylidene chloride, polyester, nylon and co-polymers thereof, to the extent that they are capable of being dyed and are preferably thermally resistant. For this reason, where non-keratinous hair fibres are employed in connection with the present invention, modacrylic fibres are preferred.

As will be appreciated, the advantages of the present invention may also extend to dyeing any keratinous substrate, including skin and nails, in addition to hair fibres. Therefore, in another aspect, the present invention also provides a method of dyeing a keratinous substrate, said method comprising the steps of: i) coating a keratinous substrate with a dye composition; and ii) directing radio frequency electromagnetic radiation having one or more frequencies from 1 MHz to 300 MHz to the coated keratinous substrate to cause heating within the keratinous substrate by dielectric loss. The radiation may be provided by any suitable device or application described herein and the dye composition may be as described below in the context of a hair dye composition, the ingredients of which may be tailored for improved compatibility with alternative keratinous substrates such as skin and nails, for instance to avoid skin-sensitivity issues.

Reference to a hair dye composition in accordance with the present invention is intended to refer to any composition which comprises one or more active hair dyeing agents, or precursors thereof, and optionally an oxidizing agent, suitable for modifying the colour of hair fibres. Preferably, the one or more active dye agents are able to penetrate the cortex of the hair shaft and replace or mask melanin contained therein. The hair dye composition may therefore be a permanent, demi-permanent, semi-permanent, and/or temporary hair dye composition. In some embodiments, the application of dielectric loss may facilitate dye uptake/penetration into the hair shaft of molecules that otherwise (given molecular size/weight/orientation) would not be able to penetrate readily into the hair shaft using conventional hair dye chemistry.

A "permanent" hair dye composition referred to herein contains an activating agent (e.g. an oxidizing agent) and one or more dye precursors, as well as usually an alkalizing agent (which also acts as a hair swelling agent). In the formation of a permanent dye composition, an activating agent may, for example, convert a primary dye precursor to an active dye agent. Alternatively or additionally, the primary dye precursor, once activated, may couple with a secondary dye precursor (also known as a coupler molecule or colour modifier) thereby producing a larger active dye agent. This process may occur inside the hair shaft meaning that larger active dye agents may be formed inside therein which are restricted or less able to diffuse out of the hair shaft during washing. Where the activating agent is an oxidizing agent, or an oxidizing agent is also present in the composition, bleaching of the hair shaft (decolourizing melanin contained in the cortex) may also occur so that lightening of the hair fibres may be achieved. Alkalizing agent is normally also employed in permanent hair dye compositions to cause swelling of the hair shaft to facilitate penetration of an oxidizing agent and/or active dye agents into the cortex of the hair shaft.

A "demi-permanent" hair dye composition referred to herein is similar to a permanent hair dye composition but typically contains an alkalizing agent which is not ammonia and contains lower concentrations of oxidizing agent compared to a permanent dye composition. The active dye agent in demi-permanent dye compositions may penetrate the cortex of the hair shaft but there is no more than partial removal of melanins in the cortex. The demi-permanent dye may therefore penetrate into the cortex of the hair fibre and mask the natural source of pigmentation, but generally cannot colour hair to a lighter shade. Active dye agents may diffuse out of the cortex, for instance, during washing and typically last 12 to 24 shampoos.

A "semi-permanent" hair dye composition referred to herein typically comprises an active dye agent but no oxidizing agent and often little or no alkalizing agent. Active dye agents present in the semi-permanent dye composition include direct dyes. The active dye agents are capable of at least partially penetrating the cortex of the hair shaft but only mask melanin therein, there being no decolourizing or solubilizing of melanin. These dyes typically last 4 to 5 shampoos.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9, 9a,10-tetrahydroanthracen-1-ylamino)-N-propylpropan-1-aminium bromide: Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyidine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

A "temporary" hair dye composition referred to herein typically only coats the external cuticle layer of the hair shaft, without any penetration of dye agent into the cortex. This is because temporary hair dye compositions generally contain dye agents which are too large to diffuse into the hair shaft. Active hair dye agents are therefore typically removed from the surface of the cuticle layer following only a single shampooing. Temporary hair dye compositions may, nevertheless, also include polymeric dye components which may be deposited on hair fibres, and which may also benefit from the advantages of the invention. Such polymeric dye components are discussed in more detail below.

In preferred embodiments, the hair dye composition used in accordance with the method of the present invention is a permanent, demi-permanent or semi-permanent hair dye composition. More preferably, the hair dye composition used in accordance with the method of the present invention is a permanent or demi-permanent hair dye composition. Most preferably, the hair dye composition used in accordance with the method of the present invention is a permanent hair dye composition.

In preferred embodiments, the hair dye composition used in step i) is a permanent or demi-permanent hair dye composition that may be prepared, preferably shortly before its use in step i) of the method, by combining a dye lotion containing one or more dye precursors and an activator solution containing an activating agent, wherein the activating agent in the activator solution converts the one or more dye precursors in the dye lotion to active dye agents. In an example embodiment, the activating agent converts a primary dye precursor (also known as primary intermediates or developers) into an activated species which subsequently couples with a secondary dye precursor (also known as secondary intermediates or couplers) to produce a larger active dye agent.

Any suitable dye precursors may be used in connection with the hair dye composition used in the present invention. As will be appreciated, where a dye lotion is provided as in embodiments of the invention, the dye precursors must be suitable for activation by the activating agent present in the activator solution.

In some embodiments, the hair dye composition used in the present invention may comprise oxidative dye precursors, which may be primary or secondary intermediates. Various secondary intermediates may be used with primary intermediates in order to obtain different shades and intensity of colouration which is desired from the hair dyeing process. Oxidative dye precursors may be free bases or the cosmetically acceptable salts thereof. Typically, the hair dye composition may comprise a total amount of oxidative dye precursors ranging up to about 12%, alternatively from about 0.1% to about 10%, alternatively from about 0.3% to about 8%, alternatively from about 0.5% to about 6%, by weight of the total composition.

Suitable primary intermediates that may be present in the hair dye composition used in the present invention include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable secondary intermediates that may be present in the hair dye composition used in the present invention include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

Any suitable activating agent may be used for preparing active dye agents provided it is functionally compatible with the one or more dye precursors selected. Preferably the activating agent is an oxidising agent. Any oxidizing agent known in the art may be used. Preferred oxidizing agents are water-soluble peroxygen oxidizing agents. As used herein, "water-soluble" means that in standard conditions at least about 0.1 g, preferably about 1 g, more preferably about 10 g of the oxidizing agent can be dissolved in 1 liter of deionized water at 25° C. The oxidizing agents are valuable for the initial solubilisation and decolorisation of the melanin (bleaching) and for accelerating the oxidation of the oxidative dye precursors (oxidative dyeing) in the hair shaft. Typically, the composition may comprise a total amount of oxidizing agents ranging from about 0.1% to about 10%, alternatively from about 1% to about 7%, alternatively from about 2% to about 5%, by weight of the total composition.

Suitable water-soluble oxidizing agents include, but are not limited to: inorganic peroxygen materials capable of yielding hydrogen peroxide in an aqueous solution. Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use. In some embodiments, the hair dye composition comprises a water-soluble oxidizing agent selected from the group consisting of hydrogen peroxide, percarbonates (which may be used to provide a source of both oxidizing agent and carbonate ions and or ammonium ions), persulphates, and mixtures thereof.

Where a dye composition is prepared from combining a dye solution and an activator solution as described herein, the concentration of activating agent may correspond to that in the activator solution before being mixed with the dye solution, or the concentration in the composition after the dye solution and activator solution have been mixed.

The dye solution and activator solution used in certain embodiments for preparation of the permanent or demi-permanent hair dye composition may be mixed in equal weight parts. The amount of activating agent may be selected so as to ensure sufficient activation of the one or more dye precursors in the dye solution. Furthermore, in the case of the permanent hair dye composition, where an oxidizing agent is employed as the activating agent, the amount of oxidizing agent may be selected so that it is sufficient for both activation of dye precursors in the dye solution and bleaching of the hair fibres, particularly where hair lightening is desired.

As discussed above, the hair dye composition used in accordance with the present invention may comprise a polymeric dye component. For example, the polymeric dye component may be: i) a cationic coloured polymer, which corresponds to a cationic polymer comprising at least one chromophore and/or at least one fluorophore either in the skeleton or as pendent group; or ii) an anionic coloured polymer, which corresponds to an anionic polymer comprising at least one chromophore and/or at least one fluorophore either in the skeleton or as pendent group.

The chromophores may be selected from the group consisting of radicals derived from nitrobenzene, azo, imine, hydrazine, phenothiazine, xanthene, phenanthridine, phthalocyanin and triarylmethane-based dyes, and those obtained from direct dyes containing a carbonyl group and mixtures thereof. The chromophores may be selected from the group consisting of radicals derived from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, and mixtures thereof.

The chromophores may be substituted with at least one amine, hydroxyl, sulfate, sulfonate, carboxylate, phosphate, phosphonate, or halide group. These chromophores may be selected from the group consisting of radicals derived from acidic nitro direct dyes, acidic azo dyes, acidic azine dyes, acidic triarylmethane dyes, acidic indoamine dyes and non-quinone acidic natural dyes, and mixtures thereof.

The chromophores may also be selected from certain derivatives of the direct dyes discussed above.

The fluorophores may be selected from the group consisting of radicals derived from di-, tetra- or hexa-sulfonated triazine-stilbenes, coumarins, imidazolines, diazoles, triazoles, benzoxazolines, biphenyl-stilbenes optical brighteners, and mixtures thereof.

A cationic coloured polymer or an anionic coloured polymer may comprise the same type of chromophore and/or fluorophore or different types of chromophores and/or fluorophores. Having a cationic coloured polymer or an anionic coloured polymer with different types of chromophores and/or fluorophores may help to cover a broad range of colour shades which can be obtained on hair which are coloured according to the method of the present wherein the first composition or the second composition comprises such a cationic coloured polymer or such an anionic coloured polymer.

Suitable cationic coloured polymers include, but are not limited to:

i. Coloured linear or branched polyethyleneimine (PEI) of the formula:

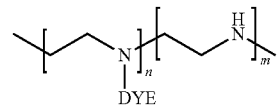

in which n and m are integers representing the degree of polymerization, wherein m/n ranges from 0 to 1,000 provided that n is different from 0 and/or m+n ranges from 50 to 20,000, alternatively from 100 to 3,500;

ii. Coloured polyallylamine hydrochloride of the formula:

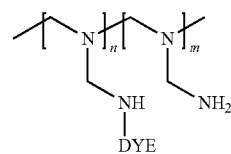

in which n and m are integers representing the degree of polymerization, wherein m/n ranges from 0 to 1,000 provided that n is different from 0 and/or m+n ranges from 50 to 20,000, alternatively from 150 to 800;

iii. Coloured polydiallyldimethylammonium chloride of the formula:

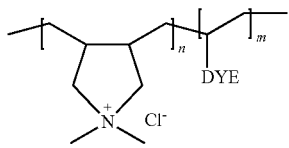

in which n and m are integers representing the degree of polymerization, wherein m/n ranges from 0 to 1,000 provided that n is different from 0 and/or m+n ranges from 50 to 20,000, alternatively from 100 to 3,500;

"DYE" in the above formulae represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

The cationic coloured polymers may be selected from linear polyethyleneimine (PEI)-Rhodamine B of the formula:

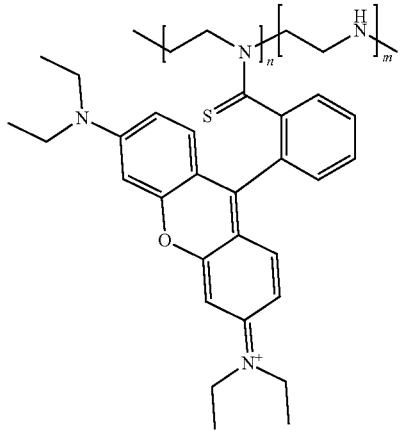

in which n and m are integers representing the degree of polymerization, wherein m/n may range from 0 to 1,000 provided that n is different from 0 and/or m+n may range from 50 to 20,000, alternatively from 100 to 3,500. These polymers may be block copolymers or random copolymers.

Suitable anionic coloured polymers include, but are not limited to polymers with the following formula:

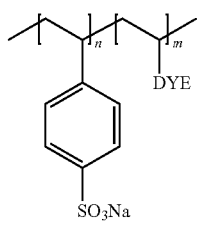

in which n and m are integers representing the degree of polymerization, wherein m/n may range from 0 to 1,000 provided that n is different from 0 and/or m+n may range from 50 to 20,000, alternatively from 150 to 500;

"DYE" in the above formula represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

As indicated above, the hair dye composition used in accordance with the present invention may also comprise alkalizing agents. Typically, the hair dye composition may comprise a total amount of alkalizing agents ranging from about 0.1% to about 10%, alternatively from about 0.5% to about 6%, alternatively from about 1% to about 4%, by weight of the total composition. Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine. Preferably, if present, the ammonium ions and carbonate ions are present in the composition at a weight ratio of from 3:1 to 1:10, alternatively from 2:1 to 1:5.

Where a non-aqueous composition is used, silicates, discussed in more detail below, may also be employed as alkalizing agents. The above-mentioned alkalizing agents also act as hair swelling agents and are typically used in connection with permanent hair dye compositions, as well as demi-permanent hair dye compositions to varying extents, where it is desired to facilitate penetration of an oxidizing agent and/or an active hair dye agent inside the hair shaft.

The hair dye composition used in accordance with the present invention may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996).

Typically, the composition may comprise a total amount of chelants ranging from at least about 0.01%, alternatively from about 0.01% to about 5%, alternatively from about 0.25% to about 3%, alternatively from about 0.5% to about 1%, by weight of the total composition. Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutarc acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative—$PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylenediamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the hair dye composition used in accordance with the invention is obtained by mixing a tint composition and a developer composition, the chelants may be incorporated in the tint composition and/or in the developer composition. A chelant is usually present in the developer composition for stability reason.

The hair dye composition used in accordance with the present invention may further comprise a conditioning agent, and/or be used in combination with a composition comprising a conditioning agent. Typically, the composition may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane ($Si(CH_3)_2$—O) units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be $(CH_3)_3Si$—O, $R_{12}(CH_3)_2Si$—O, where $R_{12}$ can be either OH or $OR_{13}$, where $R_{13}$ is a $C_1$-$C_8$ alkyl group, or a mixture of both terminal groups. These silicones are also available as preformed emulsions. Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alky chains.

Commercially available materials are known as methoxy PEG/PPG-7/3 Aminopropyl Dimethicone (e.g. Abil Soft AF100, by Degussa), or as Bis($C_{13}$-1s Alkoxy)PG Amodimethicone (e.g. DC 8500, by Dow Corning).

Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about $5\times10^6$, alternatively from about 1000 to about $3\times10^6$. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylamides substituted on the nitrogen with at least one group chosen from lower ($C_1$-$C_4$) alkyls, acrylic and methacrylic acids and esters thereof, vinylactams such as vinylpyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); copolymers of vinyl pyrrolidone and dialkylaminoalkyl acrylates or methacrylates, including polymers known as Polquaternium-11 (see Gafquat 440/734/755/755N by ISP; Luviquat PQ11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquaternium-9, Polyquaternium-12, Polyquaternium-13 Polyquaternium-14, Polyquaternium-15 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock: Catinal C-100/HC-35/HC-100/HC-200/LC-100/LC-200 by Toho; Celquat SC-240C/SC-230M by National Starch; Dekaquat 400/3000 by Dekker: Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallyamine or of dialkyldiallyammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackemium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackemium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [—$N^+(R_1)(R_2)$-$A_1$-$N^+(R_3)(R_4)$—$B_1$-][$2X^-$], in which $R_1$, $R_2$, $R_3$ and $R_4$, which may be identical or different, are chosen from aliphatic, alicyclic and arylaliphatic radicals comprising from 1 to 20 carbon atoms and from lower hydroxyalkylaliphatic radicals, or $R_1$, $R_2$, $R_3$ and $R_4$, together or separately, constitute, with the nitrogen atoms to which they are attached, heterocycles optionally comprising a second heteroatom other then nitrogen, or $R_1$, $R_2$, $R_3$ and $R_4$, are chosen from liner or branched $C_1$-$C_6$ alkyl radicals substituted with at least one group chosen from nitrile, ester, acyl and amide groups and groups of —CO—O—$R_5$-D and —CO—NH—$R_5$-D wherein $R_5$ is chosen from alkylene groups and D is chosen from quaternary ammonium groups. $A_1$ and $B_1$, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and $X^-$ is an anion derived from inorganic and organic acids. D is chosen from a glycol residue, a bis-secondary diamine residue, a bis-primary diamine residue or a ureylene group. Suitable examples include polymers known as Hexadimethrine chloride, where $R_1$, $R_2$, $R_3$ and $R_4$ are each methyl radicals, $A_1$ is $(CH_2)_3$ and $B_1$ is $(CH_2)_6$ and X=Cl; as polyquaternium-34 where $R_1$ and $R_2$ are ethyl radicals and $R_3$ and $R_4$ are methyl radicals and $A_1$ is $(CH_2)_3$ and $B_1$ is $(CH_2)_3$ and X=Br (e.g. Mexomere PAX by Chimax).

7) Polyquaternary ammonium polymers comprising repeating units of formula [—$N^+(R_6)(R_7)$—$(CH_2)_r$—NH—CO—$(CH_2)_q$—(CO)—NH—$(CH_2)_s$—$N^+(R_8)(R_9)$-A-][$2X^-$], in which $R_6$, $R_7$, $R_8$ and $R_9$ which may be identical or different, are chosen from a hydrogen atom and a methyl, ethyl, propyl, hydroxyethyl, hydroxypropyl, and —$CH_2CH_2(OCH_2CH_2)_p$OH radicals, wherein p is equal to 0 or an integer ranging from 1 to 6, wherein $R_6$, $R_7$, $R_8$ and $R_9$ do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —$CH_2$—$CH_2$—O—$CH_2$—$CH_2$—. Suitable examples include: polymers known as polyquaternium-2, where r=s=3, q=0, t=0, $R_6$, $R_7$, $R_8$ and $R_9$ are methyl groups, and A is —$CH_2$—$CH_2$—O—$CH_2$—$CH_2$ (e.g. Ethpol PQ-2 from Ethox; Mirapol A-15 by Rhodia); as polyquaternium-17 where r=s=3, q=4, t=1 $R_6$, $R_7$, $R_8$ and $R_9$ are methyl groups, and A is —$CH_2$—$CH_2$—O—$CH_2$—$CH_2$; as Polyquaternium 18, where r=s=3, q=7, t=1 Re, $R_7$, Re and $R_9$ are methyl groups, and A is —$CH_2$—$CH_2$—O—$CH_2$—$CH_2$; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370//FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care by BASF).

9) Polyamines such as Polyquart H sold by Cognis under the reference name polyethylene glycol (15) tallow polyamine.

10) Cross linked methacryloyloxy($C_1$-$C_4$)alkyltri(C1-C4) alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula $(R_{10}$—$N^+(CH_3)_2)$—$R_{11}$—$(Si(CH_3)_2$—$O)_x$—$R_{11}$—$(N^+(CH_3)_2)$—$R_{10})$, where $R_{10}$ is an alkyl derived from coconut oil, and $R_{11}$ is $(CH_2CHOCH_2O(CH_2)_3$ and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane —$(Si(CH_3)_2$—O) units within the polymer chain, with either terminal, graft or a mixture of terminal and graft aminofunctional groups.

Example functional groups are not limited to aminoethylaminopropyl, aminoethylaminoisobutyl, aminopropyl. In the case of graft polymers, the terminal siloxane units can either be $(CH_3)_3Si$—O or $R_{12}(CH_3)_2Si$—O, where $R_{12}$ can be either OH or $OR_{13}$, where $R_{13}$ is a $C_1$-$C_8$ alky group, or a mixture of both functional terminal groups. These silicones are also available as preformed emulsions. Polymer with terminal siloxane units of $(CH_3)_3Si$—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of $(R_{12}O)(CH_3)_2Si$—O where $R_{12}$ can be either OH or $OR_{13}$, where $R_{13}$ is a $C_1$-$C_8$ alky group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning: SM2059 by GE silicones). Silicones containing groups which may be ionised into cationic groups—for example silicones containing at least 10 repeating siloxane —$(Si(CH_3)_2$—O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products known as methoxy PEG/PPG-7/3 Aminopropyl Dimethicone (e.g. Abil Soft AF100 by Degussa). For example products known as Bis ($C_{13-15}$ Alkoxy) PG Amodimethicone (e.g. DC 8500 by Dow Corning).

In preferred embodiments, the cationic polymer is selected from the group consisting of polyquaternium 37, polyquaternium 7, polyquaternium 22, polyquaternium 87, and mixtures thereof; particularly from the group consisting of polyquaternium 37, polyquaternium 22, and mixtures thereof.

The hair dye composition used in accordance with the present invention may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof. Typically, the composition may comprise a total amount of surfactants ranging from about 1% to about 60%, alternatively from about 2% to about 30%, alternatively from about 8% to about 25%, alternatively from about 10% to about 20%, by weight of the total composition.

The compositions may comprise a mixture of an anionic surfactant and an amphoteric surfactant with one or more nonionic surfactants. The composition may comprise a total amount of anionic surfactant ranging from about 0.1% to about 20%, alternatively from about 0.1% to about 15%, alternatively from about 5% to about 15%, by weight of the total composition; and a total amount of amphoteric and/or nonionic components, which may range independently from each other from about 0.1% to about 15%, alternatively from about 0.5% to about 10%, alternatively from about 1% to about 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups: polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold as Miranol, as described, for example, in U.S. Pat. Nos. 2,528,378 and 2,781,354 and having the structures of: $R_2$—CON $HCH_2CH_2$—$N'(R_3)(R_4)(CH_2COO^-)$, (VI) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—$CONHCH_2CH_2$—N(B)(C) (VII) wherein B represents —CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, R$_5$ is chosen from alkyl radicals of an acid R$_5$—COOH present in coconut oil or in hydrolysed linseed oil, alkyl radicals, such as C$_7$, C$_9$, C$_{11}$ and C$_{13}$ alkyl radicals, a C$_{17}$ alkyl radical and its iso form, and unsaturated C$_{17}$ radical. These compounds are classified in the CTFA dictionary, 5$^{th}$ edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter.

A) Quaternary ammonium salts of general formula (VIII) below:

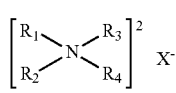
(VIII)

wherein X$^-$ is an anion chosen from halides (chloride, bromide and iodide), (C$_2$-C$_6$)alkyl sulphates, such as methyl sulphate, phosphates, alkyl and alkylaryl sulphonates, and anions derived from organic acids, such as acetate and lactate, and wherein R$_1$ to R$_4$ are as below in i) or ii).

i) Radicals R$_1$ to R$_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. R$_4$ is chosen from linear and branched alkyl radicals comprising from 16 to 30 carbon atoms. A suitable cationic surfactant is, for example, a behenyltrimethylammonium salt (for example chloride).

ii) Radicals R$_1$ and R$_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals R$_3$ and R$_4$, which may be identical or different, are chosen from linear and branched alkyl radicals comprising from 12 to 30 carbon atoms, the said alkyl radicals comprise at least one function chosen from ester and amide functions. R$_3$ and R$_4$ may be chosen from (C$_{12}$-C$_{22}$)alkylamido(C$_2$-C$_6$)alkyl and (C$_{12}$-C$_{22}$) alkylacetate radicals. A suitable cationic surfactant is, for example, a dicetyldimethyl ammonium salt (for example chloride);

B) Quaternary ammonium salts of imidazolinium of formula (IX) below:

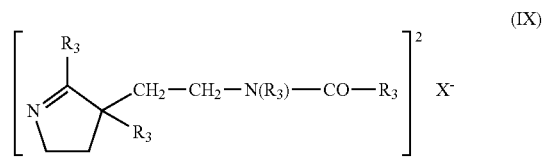
(IX)

in which R$_5$ is chosen from alkenyl and alkyl radicals comprising from 8 to 30 carbon atoms, for example fatty acid derivatives of tallow, Re is chosen from a hydrogen atom, C$_1$-C$_4$ alkyl radicals and alkenyl and alkyl radicals comprising from 8 to 30 carbon atoms, R$_7$ is chosen from C$_1$-C$_4$ alkyl radicals, Re is chosen from a hydrogen atom and C$_1$-C$_4$ alkyl radicals, and X$^-$ is an anion chosen from halides, phosphates, acetates, lactates, alkyl sulphates, alkyl sulphonates and alkylaryl sulphonates. In one embodiment, R$_5$ and Re are, for example, a mixture of radicals chosen from alkenyl and alkyl radicals comprising from 12 to 21 carbon atoms, such as fatty acid derivatives of tallow, R$_7$ is methyl and R$_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (X):

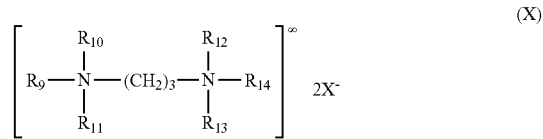
(X)

in which R$_9$ is chosen from aliphatic radicals comprising from about 16 to 30 carbon atoms, R$_{10}$, R$_{11}$, R$_{12}$, R$_{13}$ and R$_{14}$, which may be identical or different, are chosen from hydrogen and alkyl radicals comprising from 1 to 4 carbon atoms, and X$^-$ is an anion chosen from halides, acetates, phosphates, nitrates and methyl sulphates. Such diquaternary ammonium salts, for example, include propanetallowdiammonium dichloride.

D) Quaternary ammonium salts comprising at least one ester function, of formula (XI) below:

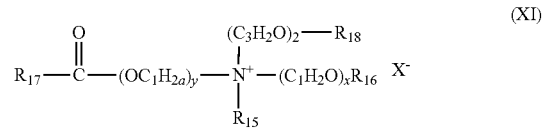
(XI)

in which: R$_{15}$ is chosen from C$_1$-C$_6$ alkyl radicals and C$_1$-C$_6$ hydroxyalkyl and dihydroxyalkyl radicals; R$_{16}$ is chosen from: a radical R$_{19}$C(O)—, linear and branched, saturated and unsaturated C$_1$-C$_{22}$ hydrocarbon-based radicals R$_{20}$, and a hydrogen atom, R$_{18}$ is chosen from: a radical R$_{21}$C(O)—, linear and branched, saturated and unsaturated C$_1$-C$_6$ hydrocarbon-based radicals R$_{22}$, and a hydrogen atom, R$_{17}$, R$_{19}$ and R$_{21}$, which may be identical or different, are chosen from linear and branched, saturated and unsaturated C$_7$-C$_{21}$ hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X— is an anion chosen from simple and complex, organic and inorganic anions; with the proviso that the sum x+y+z is from 1 to 15, that when x is 0, then $R_{16}$ is $R_{20}$ and that when z is 0, then $R_{18}$ is $R_{22}$. In one embodiment, the ammonium salts of formula (XI) can be used, in which: $R_{15}$ is chosen from methyl and ethyl radicals, x and y are equal to 1; z is equal to 0 or 1; n, p and r are equal to 2; $R_{16}$ is chosen from: a radical $R_{19}C(O)$—, methyl, ethyl and $C_{14}$-$C_{22}$ hydrocarbon-based radicals, and a hydrogen atom; $R_{17}$, $R_{19}$ and $R_{21}$, which may be identical or different, are chosen from linear and branched, saturated and unsaturated $C_7$-$C_{21}$, hydrocarbon-based radicals; $R_{18}$ is chosen from: a radical $R_{21}C(O)$— and a hydrogen atom. Such compounds are commercially available as Dehyquart by Cognis, Stepanquat by Stepan, Noxamium by Ceca, and Rewoquat WE 18 by Rewo-Witco.

The hair dye composition used in accordance with the present invention may also comprise a thickener in an amount sufficient to provide the composition with a viscosity so that it can be readily applied to the hair without unduly dripping off the hair and causing mess. Typically, the composition may comprise a total amount of thickeners ranging from at least about 0.1%, alternatively at least about 0.5%, alternatively at least about 1%, by weight of the total composition. Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one $C_8$ to $C_{30}$ fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as $C_8$-$C_{30}$ alkyl or alkenyl groups); copolymers of vinylpyrrolidone and of fatty-chain hydrophobic monomers; copolymers of $C_1$-$C_6$ alkyl acrylates or methacrylates and of amphiphilic monomers comprising at least one fatty chain; copolymers of hydrophilic acrylates or methacrylates and of hydrophobic monomers comprising at least one fatty chain, and mixtures thereof.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (I) below

$$CH_2=C(R_1)CH_2OBnR \qquad (I)$$

in which $R_1$ is chosen from H and $CH_3$, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a $(C_8$-$C_{30})$ alkyl ester or $(c_8$-$C_{30})$ oxyethylenated alkyl ester of an unsaturated carboxylic acid, wherein the hydrophilic unit of unsaturated olefinic carboxylic acid type corresponds to, for example, the monomer of formula (II) below

$$CH_2=C(R_1)COOH \qquad (II)$$

in which $R_1$ is chosen from H, $CH_3$, $C_2H_5$ and $CH_2COOH$ (i.e. acrylic acid, methacrylic, ethacrylic and itaconic acid units); and wherein the hydrophobic unit of the type such as a $(C_8$-$C_{30})$ alkyl ester or $(C_8$-$C_{30})$ oxyethylenated alkyl ester of an unsaturated carboxylic acid corresponds to, for example, the monomer of formula (III) below

$$CH_2=C(R_1)COOBnR_2 \qquad (III)$$

in which $R_1$ is chosen from H, $CH_3$, $C_2H_5$ and $CH_2COOH$ (i.e. acrylate, methacrylate, ethacrylate and itaconate units), B is an ethyleneoxy radical, n is chosen from zero and integers ranging from 1 to 100, $R_2$ is chosen from $C_8$-$C_{30}$ alkyl radicals, for example, $C_{12}$-$C_{22}$ alkyl radical. Anionic amphiphilic polymers may further be cross-linked. The crosslinking agent can be a monomer comprising a group (IV) below

$$CH_2=C< \qquad (IV)$$

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/$C_8$-$C_{30}$ alkyl methacrylate copolymers, wherein the alkyl radical is, for example, a stearyl radical.

Preferred associative polymers comprise at least one hydrophilic unit which is unsaturated carboxylic acid or its derivatives, and at least one hydrophobic unit which is a $C_8$-$C_{30}$ alkyl ester or oxyethylenated $C_8$-$C_{30}$ alkyl ester of unsaturated carboxylic acid. The unsaturated carboxylic acid is preferably acrylic acid, methacrylic acid or itaconic acid. Commercially available materials include those sold as Aculy-22 by Rohm & Haas; Permulen TR1, Carbopol 2020, Carbopol Ultrez-21 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one $C_8$-$C_{30}$ fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of $C_1$-$C_6$ alkyl acrylate or (meth)acrylate, and mixtures thereof. Commercially available materials include those sold as Carbopol 980/981/954/2984/5984 by Noveon, Synthalen M/Synthalen L/Synthalen K by 3V Sigma, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and non-ionic derivatives thereof (hydroxypropyl guar) and bio-polysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc. A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie. Another preferred polysaccharide is hydroxypropyl starch derivative, particularly hydroxypropyl starch phosphate, commercially available as Structure XL® by National Starch.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), N-vinylpyrollidone (Povidone), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/StearyVSMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth-10 phosphate, Di-cetyl phosphate and Cetearyl alcohol (available as Crodafos CES), and mixtures thereof.

The hair dye composition used in accordance with the present invention may also comprise a source of carbonate ions, carbamate ions, hydrogen carbonate ions, and mixtures thereof in a sufficient amount to reduce damage to the hair during the coloring process. Typically, the composition may comprise a total amount of a carbonate ion source ranging from about 0.1% to about 15%, alternatively from about 0.1% to about 10%, alternatively from about 1% to about 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

The hair dye composition used in accordance with the present invention may also comprise a radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process. Typically, the composition may comprise a total amount of radical scavengers ranging from about 0.1% to about 10%, alternatively from about 1% by weight to about 7%, by weight of the total composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"— in the context of radical scavengers—means particularly potassium salts, sodium salts, ammonium salts, and mixtures thereof.

The hair dye composition used in accordance with the present invention may also comprise, in addition to the alkalizing agent discussed above, a pH modifier and/or buffering agent in an amount that is sufficiently effective to adjust the pH of the composition to fall within a range from about 3 to about 13, alternatively from about 8 to about 12, alternatively from about 9 to about 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof. Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

The hair dye composition used in accordance with the present invention may further comprise a solvent. The solvent may be selected from water, or a mixture of water and at least one organic solvent to dissolve the compounds that would not typically be sufficiently soluble in water. Suitable organic solvents include, but are not limited to: $C_1$ to $C_4$ lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

In some embodiments, the solvent may be selected from the group consisting of water, ethanol, propanol, isopropanol, glycerol, 1,2-propylene glycol, hexylene glycol, ethoxy diglycol, and mixtures thereof. Typically, the composition may comprise water as a main ingredient, particularly in a total amount ranging from at least about 50%, alternatively from at least about 60%, alternatively from at least about 70%, by weight of the total composition. Typically, when present, the composition comprises a total amount of organic solvents ranging from about 1% to about 30%, by weight of the total composition.

The hair dye composition used in accordance with the present invention may also comprise further ingredients include, but not limited to: anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose.

The hair dye composition used in accordance with the present invention may be in the form of a liquid, gel, paste, cream of foam and therefore methods of coating the hair dye composition on to the one or more hair fibres in accordance with step i) of the method of the invention will depend on the rheological and flow properties of the composition that is used. For instance, where the hair dye composition is in the form of a free flowing liquid, the composition may be sprayed onto the hair. However, so that the hair dye composition is more manageable, it is expected that the hair dye composition may be more viscous so as to be in the form of a gel, paste, cream or foam which may be applied to the one or more hair fibres by means of a comb, brush or other applicator, including a tube/bottle. Any suitable means of coating the one or more hair fibres may be employed in accordance with step i) of the process.

In some embodiments, where dye and oxidizing compositions are mixed, the resultant hair dye compositions preferably have a viscosity of from about 1000 to about 60,000 cPs, alternatively from about 2000 to about 30,000 cPs, alternatively from about 3000 to about 25,000 cPs. Viscosity is measured using Brookfield viscometers with cone and plate attachment. For viscosities in the range of about 0 to about 12,000 cPs, the Brookfield DV-11 viscometer with S42 plate is used. 2 ml sample of the composition is equilibrated at 26.7° C. for three minutes before the readings are taken at 1 rpm. For viscosities in the range of about 12,000 to about 60,000 cPs, the Brookfield DV-1 viscometer with S52 plate is used. 0.5 ml sample of the composition is equilibrated for 1 minute at 26.7° C. before the readings are taken at 1 rpm.

In some embodiments, the hair dye compositions used in accordance with the presence invention are provided in the form of foam which is applied to the hair. Foam formation is typically achieved by the use of a foaming agent incorporated within the mixed composition (typically present in either the oxidizing composition or the dye composition or both) in combination with a manually operated foaming device. Such manually operated foaming devices are known in the art and include aerosols devices, squeeze foamers and pump foamers. Suitable foaming agents includes surfactants such as anionic, nonionic and amphoteric surfactants, non-ionic surfactants being preferred; polysaccharides (as described herein); polyvinyl pyrrolidone and copolymers thereof; acrylic polymers such as Acrylates copolymer (Aculyn 33) and Acrylates/Steareth-20 methacrylates (Aculyn 22); $C_{12}$-$C_{24}$ fatty acids such as stearates and mixtures thereof.

In some embodiments, the hair dye compositions used in accordance with the presence invention have an ionic strength as defined herein of less than about 1.35 mole/kg, alternatively from about 0.10 to about 0.75 mole/kg, alternatively from about 0.20 to about 0.60 mole/kg. Whilst not being bound by theory, it is believed that the ionic strength value may also affect the resultant viscosity and root adhesion properties of the hair dye composition. The ionic strength can be affected by salt resources such as the dyes, sodium sulphate, ammonium carbonate anti-oxidants and chelants such as EDDS.

The dye tends to have the greatest effect on the ionic strength and thus the amounts added in order to provide any particular shade need to be considered in terms of ionic strength as well as dye outcome in order to prevent viscosity and root adhesion problems.

The ionic strength of the hair composition is a function of the concentration of all ions present in that solution and is determined according to the formula:

$$I = \frac{1}{2}\sum_{i=1}^{n} m_i z_i^2$$

where $m_i$=molality of ion i (M=mol·/Kg H$_2$O), $z_i$=charge number of that ion, and the sum is taken over all ions in the solution. For example, for a 1:1 electrolyte such as sodium chloride, the ionic strength is equal to the concentration, but for MgSO$_4$ the ionic strength is four times higher. Generally multivalent ions contribute strongly to the ionic strength. For example the ionic strength of a mixed 0.050 M Na$_2$SO$_4$ and 0.020 M NaCl solution is: I=½((2×(+1)$^2$×0.050)+(+1)$^2$×0.020+(−2)$^2$×0.050+(−1)$^2$×0.020)=0.17 M.

The one or more hair fibres coated in step i) of the method of the invention are preferably free of any other hair treatments or solvents at the point of coating the fibres. Preferably, the hair fibres that are coated in step i) are dry at the point of coating (i.e. visibly dry or dry to the touch) where, for example, dry may correspond to less than 20 wt. %, preferably less than 15 wt. %, external water content based on the weight of the hair fibres. In some embodiments, the external water content is from 2 wt. % to 20 wt. %, more preferably 5 wt. % to 15 wt. % based on the weight of the hair fibres. In some embodiments, the method of the invention further comprises a preceding step of drying the one or more hair fibres prior to coating in step i). Drying as a part of such a preceding step may be by any suitable means.

In preferred embodiments, the internal water content of the one or more hair fibres coated in step i) is at least 1 wt. %, preferably at least 2 wt. %, more preferably at least 3 wt. %, based on the weight of the hair fibres, prior to coating with the hair dye composition.

Internal or external water content of hair fibres may be determined by thermogravimetric analysis as, for instance, described in Barba et al., Thermochimica Acta, 494 (2009), pages 136 to 140. A suitable instrument for thermogravimetric analysis includes the TG-50 by Mettler Toledo. Thermogravimetric analysis relies on determining the loss of moisture content as the temperature of a sample in increased. Other suitable methods of determining internal and external water include gas chromatography techniques, as reported in J. *Cosmet, Sci.*, 54 pages 527 to 535, as well as the use of suitable sensors, such as described in U.S. Pat. No. 7,928,739.

As discussed hereinbefore, the internal/external water content of the one or more hair fibres is believed to give rise to particular benefits. In particular, by directing radio frequency electromagnetic radiation to the coated fibres, the water molecules located within the hair shaft (i.e. the internal water content of the hair fibre) may be induced to undergo dipole rotation, leading to heating within the hair fibre following dielectric loss. This is believed to have a positive effect on the penetration of, for instance, oxidising agent and dye agents through the cuticle of the hair shaft and is also believed to accelerate the formation of active dye agents inside the hair fibre. For example, an activated primary dye precursor may undergo coupling with a secondary dye precursor (coupler molecule or chemical modifier) inside the hair shaft more quickly as a result of the energy dissipation from dielectric losses associated with internal water molecules in comparison to heat applied from an external source. The external water content of the hair fibres may also further promote the dyeing process as a result of energy dissipation at the surface of the hair fibres which may also assist with penetration of the cuticle of the hair shaft by dye agents and accelerating the activation of dye precursors.

Once the one or more hair fibres have been coated with hair dye composition in accordance with step i) of the method of the invention, the coated fibres may be immediately exposed to radio frequency electromagnetic radiation in accordance with step ii) of the method. However, in preferred embodiments, the one or more coated hair fibres are left for a period of time which is sufficient, for instance, to allow impregnation of the hair dye composition into the one or more hair fibres before being subjected to radio frequency electromagnetic radiation in step ii). Preferably, said period of time is from 5 seconds to 500 seconds, preferably 25 seconds to 250 seconds, more preferably from 50 seconds to 100 seconds.

In step ii) of the method of the invention, radio frequency electromagnetic radiation is directed to the one or more coated hair fibres to cause heating within the one or more coated hair fibres by dielectric loss. The radio frequency electromagnetic radiation suitably used in accordance with the present invention has one or more frequencies from 1 MHz to 300 MHz. In preferred embodiments, the radio frequency electromagnetic radiation employed in connection with the invention has one or more frequencies of from 1 MHz to 100 MHz, more preferably from 5 MHz to 75 MHz and even more preferably from 10 MHz to 50 MHz.

The coated fibres may be subjected to radio frequency electromagnetic radiation for any suitable period of time to cause heating by dielectric loss within the hair fibre. Preferably, the one or more coated hair fibres are subjected to radio frequency electromagnetic radiation in step ii) for a period of time which is from 0.5 to 30 seconds, preferably 1 to 20 seconds, more preferably from 5 to 10 seconds. Preferably, the temperature of the one or more coated hair fibres does not exceed 100° C. as a result of heating through dielectric losses in step ii), more preferably the temperature of the one or more coated hair fibres does not exceed 90° C., as for instance measured using an IR camera.

The effective radiated power of the radio frequency electromagnetic radiation may be selected so as to afford adequate dielectric loss when coated fibres are exposed to the radio frequency electromagnetic radiation to provide heating over a suitable exposure timescale. The effective radiated power of the radio frequency electromagnetic radiation used in the method of the present invention may suitably be from 10 W to 1000 W, although when intended for use in a domestic setting range of effective radiated power may be lower, for example 10 W to 500 W. In preferred embodiments, the effective radiated power of the radio frequency electromagnetic radiation may be from 25 W to 250 W, more preferably from 50 to 150 W.

The frequency and/or effective radiated power of the radio frequency electromagnetic radiation may be variable or substantial constant during step ii) of the method of the invention. Preferably, frequency and/or effective radiated power of the radio frequency electromagnetic radiation are kept substantially constant.

In accordance with the method of the present invention, radio frequency electromagnetic radiation is directed to the coated hair fibres so as to cause heating within the one or more coated hair fibres by dielectric loss. As will be appreciated, given the relatively large wavelength of radio frequency electromagnetic radiation, the step of directing radio frequency electromagnetic radiation to the coated hair fibres is dominated by near field rather than far field characteristics.

Radio frequency electromagnetic radiation may be provided by any suitable device which is capable of generating radio frequency radiation, preferably within an enclosed region in which hair fibres may be temporarily located. As will be appreciated, it is desirable to substantially eliminate transmittance of radio frequency electromagnetic radiation beyond an enclosed environment (i.e. so as to avoid transmitting radio frequency electromagnetic radiation to the wider environment and exposing materials other than the coated hair fibres).

In some embodiments, the radio frequency electromagnetic radiation is provided by means of a device supplied with an alternating electrical current and comprising a radio frequency signal generator adapted for directing radio frequency electromagnetic radiation to hair fibres. Preferably, radio frequency radiation is transmitted in a region defined by a pair of plate electrodes, including parallel and non-parallel plate electrodes, preferably parallel plate electrodes. For example, a device may include a radio frequency signal generator comprising plate electrodes in between which hair fibres may be positioned to allow radio frequency electromagnetic radiation to be directed thereto. Where a pair of plate electrodes is used for supplying the radiofrequency electromagnetic radiation, it will be understood that the radio frequency electromagnetic radiation will be substantially confined to a zone in between the plate electrodes.

In preferred embodiments, the device used for providing radio frequency electromagnetic radiation is a portable handheld appliance. As will be appreciated, by using a portable handheld appliance to provide the radio frequency electromagnetic radiation, the method of the invention can be implemented in a variety of settings, including a domestic setting, at the convenience of the user. Such a portable handheld appliance may, for instance, comprise first and second opposing arms and be configured to generate radio frequency electromagnetic radiation in a region between the opposing arms such that hair fibres may be positioned in said region to allow radio frequency electromagnetic radiation to be directed to the hair fibres.

In another aspect, the present invention provides a handheld hair dyeing appliance comprising a radio frequency signal generator and first and second opposing arms, wherein the appliance is configured to generate radio frequency electromagnetic radiation in a region between the opposing arms when the appliance is supplied with an alternating electrical current; and wherein the appliance is adapted such that one or more hair fibres coated with a hair dye composition may be positioned in the region between the first and second opposing arms to allow radio frequency electromagnetic radiation to be directed to the coated hair fibres to cause heating within the one or more coated hair fibres by dielectric loss.

In the handheld appliance discussed above, first and second opposing arms may, for instance, each comprise a plate electrode such that electromagnetic radiation may be generated between the plates of the opposing arms. Preferably, first and second opposing arms are movable between a closed position in which a contacting surface of the first arm is adjacent a contacting surface of the second arm and an open position in which the contacting surfaces of each arm are spaced apart.

Having movable arms is advantageous since it allows the user to more easily secure a section of coated hair fibres between contacting surfaces of the arms and to direct radio frequency radiation to the section of coated hair fibres held in place between the opposing arms. By moving the appliance from one section of coated hair fibres in the axial direction of the hair fibres whilst the arms are in the closed position, consecutive sections of the coated hair fibres may pass through the region between the opposed arms so that radio frequency electromagnetic radiation is directed over a length of the coated hair fibres. In this manner, electromagnetic radiation may be directed to the coated hair fibres using a similar action to that which is commonly employed for straightening hair between heating plates of a conventional straightening iron.

The contacting surfaces of the first and second arms may each correspond to a portion of the arm or portion of an electrode plate associated with the arm. The contacting surfaces of the arms may also together represent a means for temporarily enclosing a region in which coated hair fibres may be located when the first and second arms are in the closed position.

In addition, the handheld appliance may be provided with a control system configured to only allow radio frequency electromagnetic radiation to be generated by the generator when the first and second arms are in the closed position. A control switch may thus be employed in connection with the control system to provide a signal when the arms are in the closed position. An LED located on an external surface of the handheld appliance may also be utilised in connection with the control system which emits light in response to the arms being in the closed position, and radio frequency electromagnetic radiation being generated, so as to provide an indication to the user during operation of the appliance.

Where a control system is employed, in addition to control electronics and a power supply unit, the system may include a power actuator and a power sensor so that the control system may be configured to vary the electrical power supplied to the appliance to maintain the radio frequency power as part of a feedforward control pathway. The power actuator could include a triac and/or any suitable means for controlling power output to the radio frequency signal generator. In some examples, the power actuator is a constant current source, and only the voltage output to the radio frequency signal generator is varied.

The power sensor measures the electrical power output by the power actuator, and provides this measurement of power to the control electronics. An RF sensor for measuring RF reflection or a temperature sensor may be used to determine dielectric, energy adsorption or temperature parameters of the hair during operation. The control electronics (which may include a PID (proportional, integral, derivative) controller) control the power actuator based on a measured RF reflection or temperature parameter received from the RF sensor or temperature sensor and the power measurement of the power output by the power actuator received from the power sensor. These measurements are used by the control electronics to control the power output by the power actuator in order to try and reach a target RF level of RF reflection or target temperature parameter of the appliance in operation defined, for instance, by a user via a user interface.

In some embodiments of the method of the present invention, directing radio frequency electromagnetic radiation to the coated hair fibres in step ii) involves positioning the radio frequency signal generator of a handheld appliance, such as that described above, at one section of the one or more coated hair fibres and moving the appliance in the axial direction of the one or more coated hair fibres so as to direct radio frequency electromagnetic radiation over a length of the one or more coated hair fibres. In some embodiments, such an appliance is moved in the axial direction over a length of the one or more coated hair fibres at a rate of from 1 to 100 mm/sec, preferably at a rate of from 1 to 50 mm/sec, more preferably at a rate of from 2 to 20 mm/sec, most preferably at a rate of from 2 to 8 mm/sec.

As is evident, use of an appliance in this manner can confer significant time savings in achieving an effective dye result compared to conventional hair dyeing processes, as illustrated in the examples below. Furthermore, by reducing the effective dyeing time, the exposure of the hair to potentially damaging hair dye components (for example, oxidizing agents such as hydrogen peroxide) may be reduced and the negative impacts of such components minimized.

In another aspect, the present invention provides a kit comprising: i) a hair dye composition; ii) a handheld appliance for directing radio frequency electromagnetic radiation to one or more hair fibres; wherein the handheld appliance comprises a radio frequency signal generator adapted for directing radio frequency electromagnetic radiation to hair fibres when the appliance is supplied with an alternating electrical current; and iii) instructions for use of the hair dye composition in coating one or more hair fibres and use of the handheld appliance for directing radio frequency electromagnetic radiation to the one or more coated hair fibres together as part of a hair dyeing process.

The hair dye composition and handheld appliance used in this aspect of the invention may be as described hereinbefore. As will be appreciated, the kit may include various packaging and the instructions for use of the hair dye composition may be printed on a surface of the packaging or provided separately, for instance as a printed booklet or leaflet.

In still another aspect, the present invention provides a kit comprising: i) a hair dye composition; ii) an applicator for coating one or more hair fibres with a hair dye composition; and iii) a handheld appliance for directing radio frequency electromagnetic radiation to one or more hair fibres coated with a hair dye composition; wherein the handheld appliance comprises a radio frequency signal generator adapted for directing radio frequency electromagnetic radiation to hair fibres when the appliance is supplied with an alternating electrical current.

The hair dye composition and handheld appliance used in this aspect of the invention may be as described hereinbefore. As will be appreciated, the kit may include various packaging and the instructions may be printed on a surface of the packaging or provided separately, for instance as a printed booklet or leaflet. For example, the kit may be presented in a single package comprising separate containers, such as plastic or aluminium bottles, for a tint composition, a developer composition, and optionally a conditioner, a colour refresher or other hair treatment product, instructions for use, and gloves.

The applicator for coating one or more hair fibres may take any suitable form such as a brush, comb, dispensing tube/bottle with dabber or simply a nozzle attached to a container. The applicator may be configured to assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used.

Combs and brushes can be adapted in order to achieve particular effects, whether it may be quick and even coverage or root/hairline touch up, or highlights or streaks. Alternatively, a container for the hair dye composition, or a component thereof, may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The present invention may be provided in a variety of packaging devices and/or dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then dispensed from the device and applied to the consumer's hair by an application means.

For example, a developer may be stored in a container such as a bottle, tube, aerosol, or a sachet and the dye lotion separately stored in an additional compartment within the developer container or more preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the oxidizing component and the dye component by any means. This may simply involve the use of a mixing bowl into which the compositions are dispensed and then mixed, preferably using a mixing means such as a tool.

Alternatively, it may involve the addition of one of the compositions into the container of the other composition (typically the dye composition is added to the oxidizing composition), followed by manual shaking or mixing with a tool. Another system involves the perforation or displacement of a seal located between the separate compartments of the dye and oxidizing composition within a single container or sachet followed by manual mixing within the container or in a separate and or additional container.

In yet another aspect, the present invention provides a hair dye dispensing handheld appliance for dyeing hair fibres comprising: i) a dispenser for dispensing a hair dye composition to coat one or more hair fibres; and ii) a radio frequency signal generator adapted for directing radio frequency electromagnetic radiation onto hair fibres when the appliance is supplied with an alternating electrical current; wherein the handheld appliance is configured for dispensing hair dye composition to coat one or more hair fibres and for directing radio frequency electromagnetic radiation to the coated hair fibres to cause heating of the coated hair fibres by dielectric loss.

The handheld appliance according to this aspect of the invention may be as described for the handheld appliance discussed hereinbefore but additionally comprising means for dispensing a hair dye composition. For example, the appliance may include a control switch which may be associated with a dispenser for dispensing hair dye composition. Thus, the appliance according to this aspect of the invention may be particularly convenient since it can be utilized in both steps of the method of the invention.

Preferably, the handheld appliance according to this aspect further comprises an integral compartment for holding hair dye composition which is in fluidic communication with a dispenser. For example, the integral compartment and dispenser may be associated with an one or both of first and second arms of the handheld appliance as in embodiments described hereinbefore. The integral compartment for holding hair dye composition may be associated with a door or other such temporary opening through which hair dye composition may be introduced to the compartment.

The integral compartment for holding hair dye composition may also be associated with other openings through which hair dye composition may be dispensed by the dispenser. Such openings may be provided on an upper surface of an arm of the handheld appliance which includes the integral compartment. In another example, such openings may be provided adjacent to one of the pair of electrode plates, for instance at a leading edge of the arm which includes the integral compartment, so that hair dye composition may, for example, be dispensed onto hair fibres, following which coated fibres may be exposed to radio frequency electromagnetic generated by the electrode plates, during a single movement of the handheld appliance relative to the hair.

In still another aspect, the present invention provides a use of radio frequency electromagnetic radiation for reducing the effective dye-treatment time for hair fibres using a hair dye composition by subjecting hair fibres coated and impregnated with hair dye composition to radio frequency electromagnetic radiation.

In a further aspect, the present invention provides a use of radio frequency electromagnetic radiation, as part of a hair heating process, for reducing heat damage of one or more hair fibres during heating thereof in comparison to convection heating. Preferably, at least a portion of the one hair fibres which are heated are coated with a hair dye composition.

The present invention will now be described by reference to the figures and the below examples, wherein.

Figure 1:
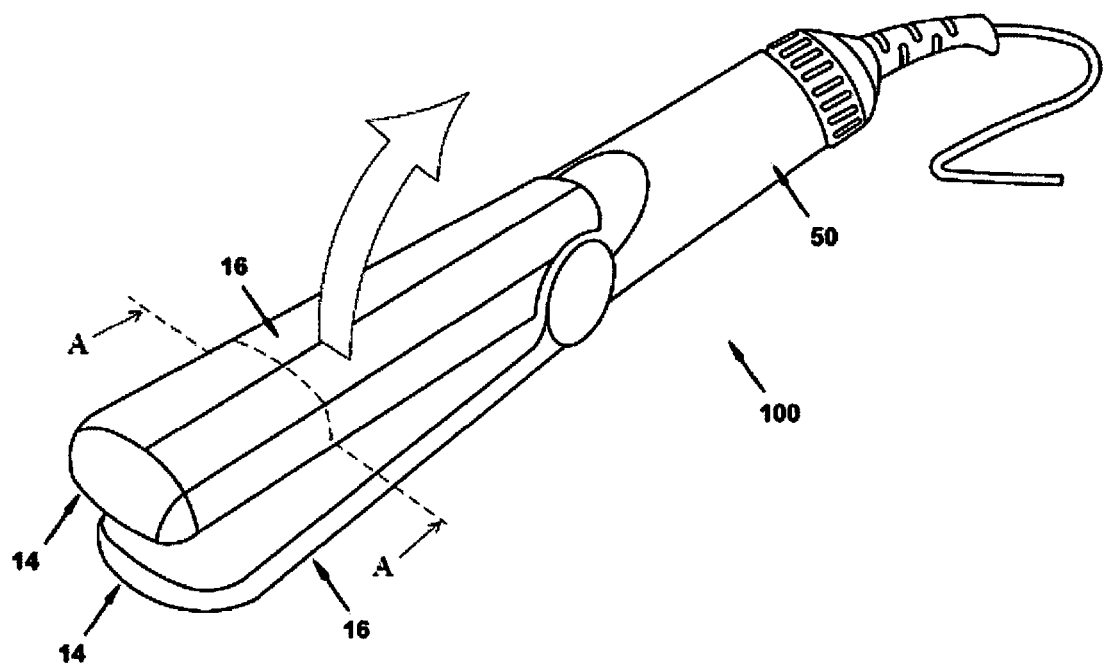
FIG. 1 shows a perspective view of an example embodiment of a handheld appliance for use with the invention.

FIG. 1 shows an example handheld appliance 100 comprising an elongate body 50 which forms a handle for a user to grip the appliance. First and second opposing arms 16 are attached to the body 50. The arms 16 are hinged together at one end where they are attached to the body 50. Each arm 16 has an electrode plate 14 associated therewith, which may include a contact surface. The arms 16 are moveable between a closed position in which a contacting surface of the first arm is adjacent a contacting surface of the second arm and an open position in which the contacting surfaces of each arm are spaced apart. FIG. 1 depicts opening of the arms from the closed position by movement of the arms in the outward direction, shown by the arrow in the case of the upper arm 16.

In the arrangement shown in FIG. 1, a radio frequency electromagnetic radiation zone (not shown) may be formed between the two opposing arms 16 when, for instance, in the closed position. In particular, the appliance may be configured so as to only generate radio frequency electromagnetic radiation when the arms 16 are in the closed position so that radio frequency electromagnetic radiation is only generated when required and to reduce leakage of radio frequency electromagnetic radiation beyond the zone formed between the two opposing arms 16.

Figure 4:
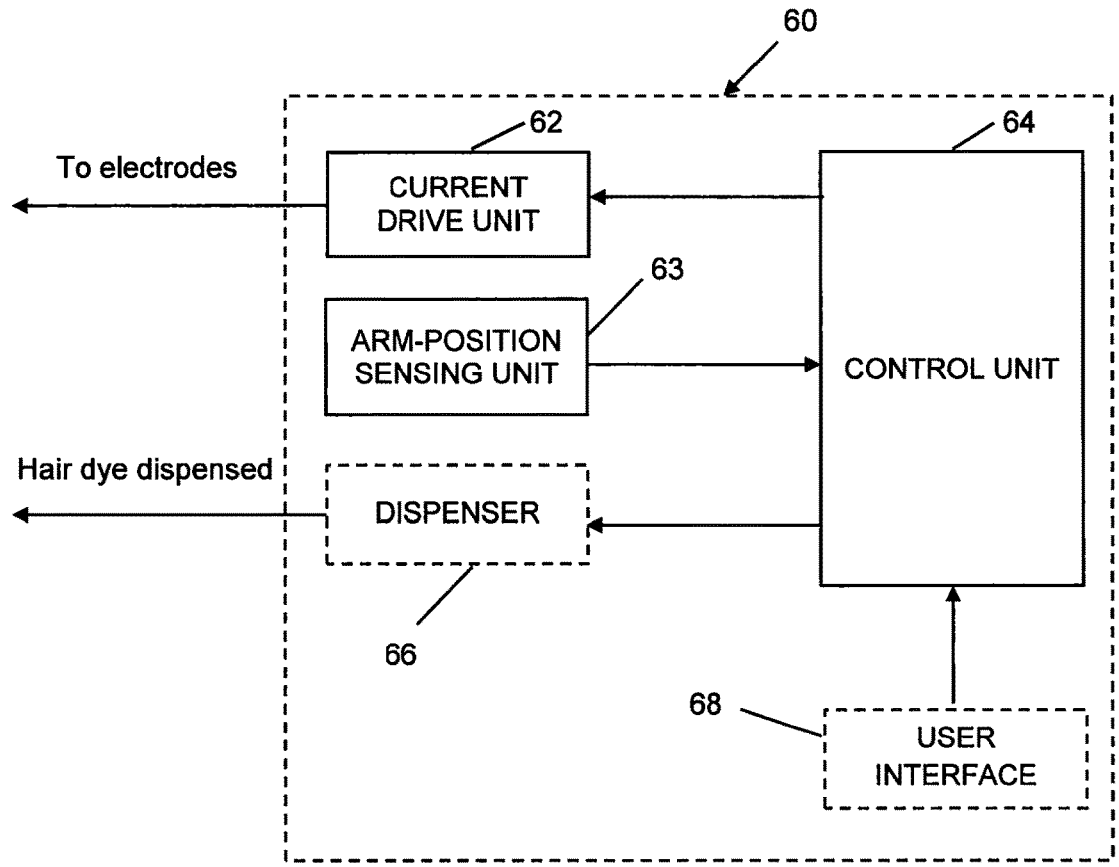
FIG. 4 shows schematic illustration of an example control system which may be used in connection with the handheld appliance for use with the invention.

The handheld appliance 100 may be provided with a control system, as illustrated schematically in FIG. 4, and configured to only allow radio frequency radiation to be generated when the arms 16 are in the closed position. A contact switch (not shown) may thus be employed which is operable to provide a signal to the control system verifying that the arms 16 are in the closed position. An LED located on an external surface of the handheld appliance 100 (not shown) may also be utilised in connection with the control system which emits light in response to the arms 16 being in the closed position, and radio frequency electromagnetic radiation being generated, so as to provide an indication to the user during operation of the appliance 100.

Figure 2:
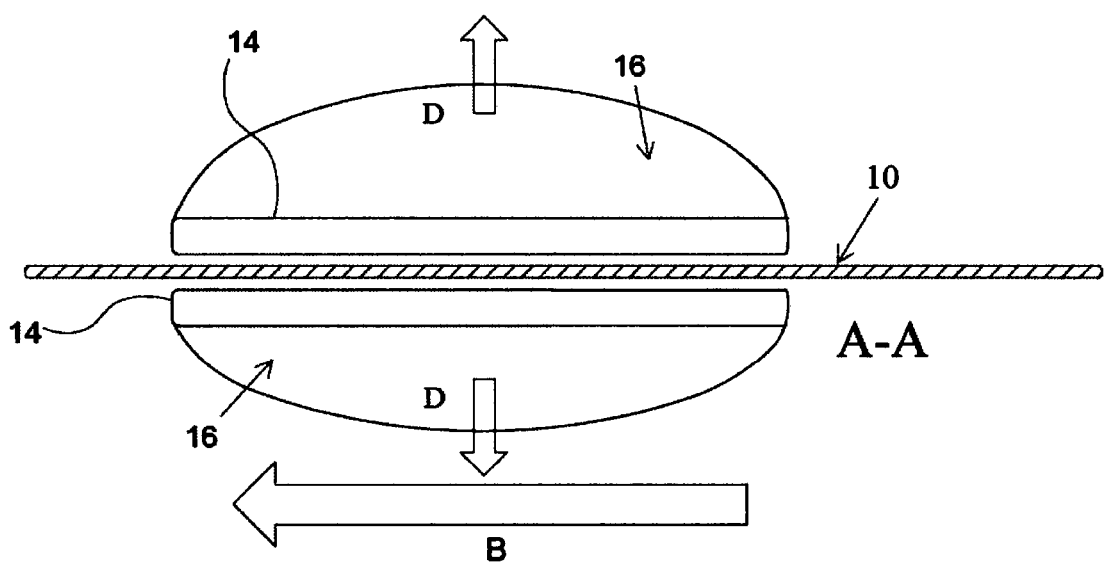
FIG. 2 shows a cross-section of the example embodiment of a handheld appliance shown in FIG. 1 along line A-A.

FIG. 2 shows a cross-section through first and second opposing arms 16 of the example handheld radio frequency generating appliance of FIG. 1 along line A-A, when the arms 16 are in the closed position. The arms 16 are moveable to an open position in the direction of arrows D. The pair of plate electrodes 14 define a radio frequency electromagnetic radiation zone where radio frequency electromagnetic radiation may be generated between electrode plates 14.

FIG. 2 shows the handheld appliance being used in the manner of a hair straightener. The coated hair 10 is clamped between the electrode plates 14. The appliance is moved relative to the hair in the direction of arrow B. As the coated hair passes through the radio frequency electromagnetic radiation zone between the electrode plates 14, the hair is exposed to radio frequency electromagnetic radiation and heated as a result of dielectric loss. As soon as a section of the coated hair exits the radio frequency electromagnetic radiation zone between the electrode plates 14, no further exposure to radiation occurs and therefore no further heating of this section takes place. Sections of hair are therefore exposed to radio frequency electromagnetic radiation and heated momentarily as the hair passes through the radio frequency electromagnetic radiation zone.

Figure 3:
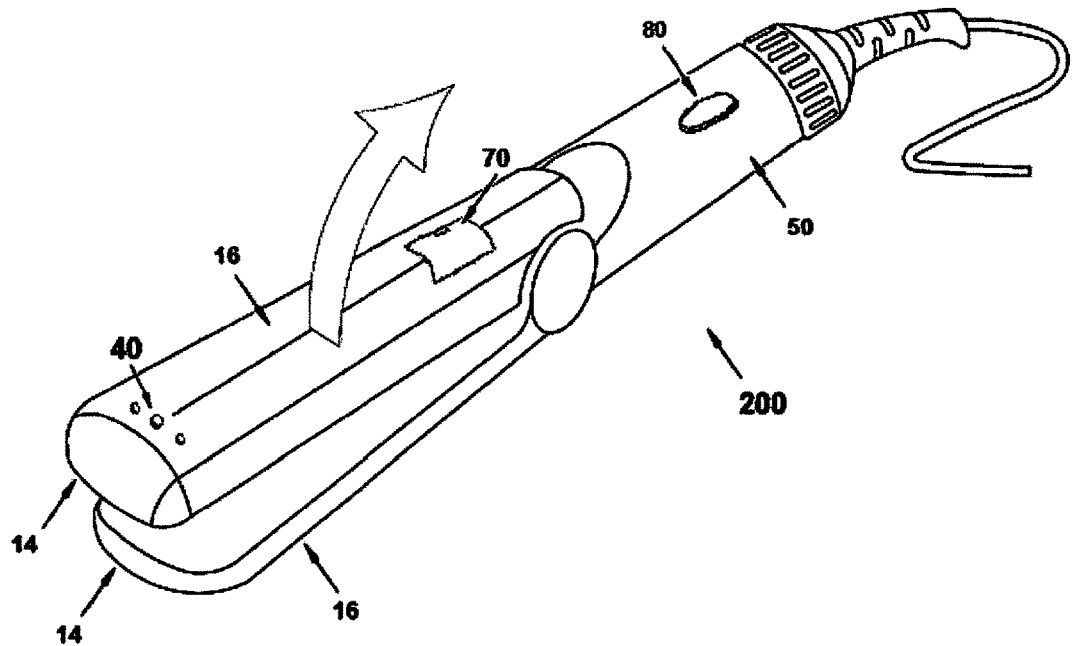
FIG. 3 shows a perspective view of an example embodiment of a handheld appliance comprising means for dispensing hair dye composition for use with the invention.

FIG. 3 shows an example of a hair dye dispensing handheld appliance 200 comprising first and second opposing arms 16, each of which having an electrode plate 14 associated therewith capable of generating radio frequency electromagnetic radiation as in the arrangement shown in FIG. 1 and discussed hereinbefore. In the arrangement shown in FIG. 3, one arm 16 comprises an integral compartment in which hair dye composition may be deposited via door 70, which may be opened and closed by the user, as necessary. The compartment is associated with dispensing openings 40 which allow hair dye composition to be dispensed therethrough. On the body 50 of the handheld appliance 200 is provided a dispensing control switch 80 which may be associated with a dispenser (not shown) which is in fluidic communication with the contents of the compartment.

When dispensing control switch 80 is actuated by the user, fluid in the compartment incorporated within the arm 16 of the handheld appliance 200 is caused to be dispensed from the dispensing openings 40. Hair dye dispensing handheld appliance 200 may be used for dispensing hair dye composition to the hair fibres and for directing radio frequency electromagnetic radiation to the coated fibres in the manner described for the appliances shown in FIGS. 1 and 2.

FIG. 4 is a schematic illustration of a control circuit 60 suitable for use with the electrode plates 14 and/or a dispenser of the appliances according to FIGS. 1 and 3. The control circuit 60 includes a current drive unit 62 operable to supply alternating electrical current to each of the electrode plates 14 associated with the opposing arms 16 of the handheld appliance shown in FIGS. 1 and 3. The control circuit 60 includes an arm-position sensing unit 63 operable to generate a signal representative of (or dependent on) the arms 16 of the handheld appliance shown in FIGS. 1 and 3 being in the closed position. The current drive unit 62 and arm-position sensing unit 63 are both connected to a control unit 64 (e.g. a suitably programmed microprocessor). The control circuit 60 may also optionally include a user interface 68 and dispenser 66 operable to cause dye composition to be dispensed from dispensing openings 40 of the handheld appliance shown in FIG. 3.

In use, the arm-position sensing unit 63 generates a signal representative of (or dependent on) the arms 16 of the handheld appliance shown in FIGS. 1 and 3 being in the closed position based on a sensor operable to determine whether the arms 16 are in the closed position, and supplies this signal to the control unit 64. The arm-sensing unit 63 may correspond to a contact switch which may, for instance, be located at the hinge of the arms 16 where they are attached to the body 50 in the handheld appliance shown in FIGS. 1 and 3. Where a signal is received from the arm-position sensing unit 63 indicating that the arms 16 are in the closed position, the control unit 64 causes the current drive unit 62 to supply alternating electrical current to the plate electrodes 14, thus causing radio frequency electromagnetic radiation to be generated in the zone between the plates 14.

A user interface 68 (e.g. control switch 80 in FIG. 3) may be provided, coupled to the control unit 64, to enable the user to selectively dispense hair dye where a hair dye dispensing appliance 200, as shown in FIG. 3, is used. In use, the user interface 68 supplies a signal to the control unit 64, for instance as the control switch 80 is actuated, the control unit 64 causes the dispenser 66 to dispense hair dye from dispensing openings 40.

EXAMPLES

In each of the examples below, a bleached Yak hair sample (tress) was employed for the treatment. Each Yak hair sample was derived from the same source and the same total sample weight and length was employed in each experiment. For each of the experiments in the examples below, the same hair dye composition was employed, and is described below.

A ColorFlex EZ spectrophotometer colour measurement instrument was employed for analysing the treated samples produced by the following experiments. This spectrophotometer employs a xenon flash lamp to illuminate the sample before relative intensities of light at different wavelengths along the visible spectrum (400-700 nm) are analyzed to produce numeric results indicative of the colour of the sample. The numeric results assimilated in connection with the below experiments include absolute colour scale parameter values, (L*, a*, b*); colour difference scale parameter values (derived from comparison with a standard), (ΔL*, Δa*, Δb*); colour difference index parameter values (ΔE, ΔE*, ΔEcmc).

L* represents the lightness of the colour, a* indicates the green/red colour axis and b* the blue/yellow colour axis. Overall color change is represented by ΔE where ΔE is defined by the following formula:

$$\Delta E = [(\Delta L^*)^2 + (\Delta a^*)^2 + (\Delta b^*)_2]^{1/2}$$

Example 1—Dyeing Hair with Heating Supplied by Radio Frequency Radiation

A sample of yak hair was coated with an aqueous hair dye composition corresponding to 1:1 mixture by weight of a Dye Lotion and an Activator Solution having a composition as indicated in the Table 1 below. Once applied, the hair dye composition was left to soak on the hair fibres for 1 minute. After soaking, the coated hair fibres were subjected to electromagnetic waves of 13.1 Mhz frequency generated by a device operating at resonance resulting in heating of the coated hair fibres to a temperature of 85° C. using IR camera measurement.

Figure 5:
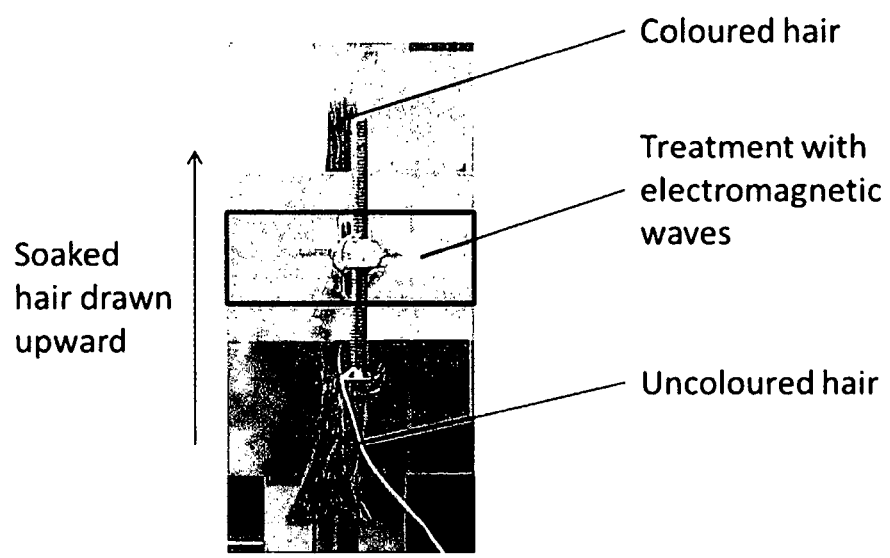
FIG. 5 shows an apparatus set-up used in connection with the examples.

The radio frequency generating device was set in a secured position as illustrated in FIG. 5 with the sample of coated hair fibres positioned so as to be exposed to radio frequency radiation on operation of the device over a section of the length of the coated hair fibres. During operation of the device, the hair sample was drawn upwards so that consecutive sections over the length of the coated hair fibres were subsequently exposed to radio frequency radiation. The sample of hair was drawn through an area of space exposed to radio frequency radiation by the radio frequency generating device at a rate of 3 mm/sec.

After the sample of coated hair fibres had been exposed to radio frequency radiation over the entire length of the coated area by the radio frequency generating device the hair sample was immediately washed using warm water and allowed to equilibrate at 50% relative humidity (RH) and 23° C. in a suitable environmental chamber. The hair sample was then measured using a Colorfex EZ Spectrophotomer, at 5 points along the length of the sample (30, 60, 90, 120, 150 mm from one end). Results are provided in Tables 2 and 3 below.

TABLE 1

| Composition | mass [g] (Total 50 g) |
|---|---|
| Dye Lotion | |
| Toluene diamine sulfate | 0.570 |
| 4-Amino-2-Hydroxytoluene | 0.280 |
| Sodium Sulfite | 0.050 |
| Hexylene Glycol | 1.000 |
| Butyl Carbitol | 2.000 |
| Ammonium chloride | 1.100 |
| Sodium Chloride | 0.050 |
| Ascorbic Acid | 0.500 |
| α-Tocopherol | 0.200 |
| Sodium Lauryl Sulfate | 3.335 |
| Sodium Hydroxide | 0.400 |
| Aculyn 22[1] | 0.750 |
| Water | 39.765 |
| Activator Solution | |
| H$_2$O$_2$ (50%) | 6.000 |
| EDTA | 0.010 |
| Aculyn 22[1] | 1.000 |
| Water | 43.99 |

[1]Aculyn 22 is a Rheology Modifier/Stabilizer anionic hydrophobically modified alkali-soluble acrylic polymer emulsion (HASE) obtained from Dow Chemical.

Comparative Example 2—Dyeing Hair with No Heating Above Ambient Temperature

The experiment according to Example 1 was repeated except that no heating of the coated hair sample was performed. Following soaking, the coated hair sample was left for 15 minutes at room temperature before being washed, dried and analysed as described for Example 1. Results are provided in Tables 2 and 3 below.

Comparative Example 3—Dyeing Hair with Heating Supplied by Straightening Iron The experiment according to Example 1 was repeated except that, following soaking, heating of the coated hair sample was performed using a straightening iron (GHD Platinum Styler) with ceramic plates heated to a temperature of 185° C. The hair sample was contacted and drawn through the heated plates of the straightening iron at a rate of 5 mm/sec. The treated hair sample was then washed, dried and analysed as described for Example 1. Results are provided in Tables 2 and 3 below.

Comparative Example 4—Dyeing Hair with Heating Supplied by Microwave

The experiment according to Example 1 was repeated except that, following soaking, heating of the coated hair sample was performed in a conventional microwave oven (100 W) for 10 seconds. The treated hair sample was then washed, dried and analysed as described for Example 1. Results are provided in Tables 2 and 3 below.

TABLE 2

| Example No. (Distance from end of hair sample, mm) | L* | a* | b* | ΔL* | Δa* | Δb* | ΔE* | ΔE CMC | ΔE CMC (l:c) |
|---|---|---|---|---|---|---|---|---|---|
| 1 (30) | 25.89 | 19.69 | −8.62 | −39.4 | 19.61 | −18.55 | 47.76 | 37.62 | 2.00:1.00 |
| 2 (30) | 9.97 | 31.95 | −15.41 | −55.32 | 31.86 | −25.34 | 68.68 | 52.52 | 2.00:1.00 |
| 3 (30) | 23.28 | 18.06 | −3.44 | −42.01 | 17.97 | −13.37 | 47.61 | 33.31 | 2.00:1.00 |
| 4 (30) | 23.84 | 19 | −7.69 | −41.45 | 18.92 | −17.62 | 48.85 | 36.85 | 2.00:1.00 |
| C² (30) | 65.29 | 0.09 | 9.93 | 65.29 | 0.09 | 9.93 | | | |
| 1 (60) | 22.3 | 21.22 | −8.71 | −43.64 | 21.15 | −18.13 | 51.77 | 39.08 | 2.00:1.00 |
| 2 (60) | 8.87 | 33.07 | 15.44 | −57.07 | 32.99 | −24.86 | 70.45 | 53.31 | 2.00:1.00 |
| 3 (60) | 28.04 | 16.34 | −2.88 | −37.9 | 16.27 | −12.3 | 43.04 | 30.61 | 2.00:1.00 |
| 4 (60) | 19.19 | 21.38 | −7.66 | −46.75 | 21.3 | −17.08 | 54.13 | 39.03 | 2.00:1.00 |
| C² (60) | 65.94 | 0.08 | 9.42 | 65.94 | 0.08 | 9.42 | | | |
| 1 (90) | 21.25 | 21.51 | −8.67 | −44.97 | 21.46 | 18.12 | 53.02 | 39.47 | 2.00:1.00 |
| 2 (90) | 7.71 | 32.89 | −15.15 | 58.51 | 32.83 | −24.6 | 71.46 | 53.25 | 2.00:1.00 |
| 3 (90) | 31.16 | 15.02 | −2.64 | −35.06 | 14.97 | −12.09 | 39.99 | 28.92 | 2.00:1.00 |
| 4 (90) | 18.45 | 21.35 | −6.87 | −47.77 | 21.3 | −16.32 | 54.79 | 38.67 | 2.00:1.00 |
| C² (90) | 66.22 | 0.05 | 9.45 | 66.22 | 0.05 | 9.45 | | | |
| 1 (120) | 20.69 | 22.14 | −8.97 | −45.31 | 22.1 | −18.39 | 53.66 | 40.13 | 2.00:1.00 |
| 2 (120) | 7.39 | 32.16 | −14.84 | −58.61 | 32.12 | −24.27 | 71.1 | 52.63 | 2.00:1.00 |
| 3 (120) | 27.95 | 16.39 | −3.07 | −38.05 | 16.35 | −12.49 | 43.26 | 30.8 | 2.00:1.00 |
| 4 (120) | 18.78 | 21.35 | −6.97 | −47.22 | 21.31 | −16.39 | 54.34 | 38.63 | 2.00:1.00 |
| C² (120) | 66 | 0.04 | 9.42 | 66 | 0.04 | 9.42 | | | |
| 1 (150) | 22.84 | 21.13 | −8.67 | 43.44 | 21.03 | −18.45 | 51.67 | 39.14 | 2.00:1.00 |
| 2 (150) | 7.92 | 32.33 | 14.51 | −58.37 | 32.23 | −24.28 | 70.96 | 52.61 | 2.00:1.00 |
| 3 (150) | 27.57 | 16.62 | −3.39 | −38.71 | 16.51 | −13.16 | 44.1 | 31.49 | 2.00:1.00 |
| 4 (150) | 15.28 | 23.73 | −7.59 | −51.01 | 23.63 | −17.36 | 58.84 | 41.49 | 2.00:1.00 |
| C² (150) | 66.29 | 0.1 | 9.77 | 66.29 | 0.1 | 9.77 | | | |

²Control - untreated Yak hair sample

TABLE 3

| Example No. | L (mean) | a (mean) | b (mean) | dE (mean) |
|---|---|---|---|---|
| 1 | 22.59 | 21.14 | −8.73 | 51.58 |
| 2 | 8.37 | 32.48 | −15.07 | 70.53 |
| 3 | 27.60 | 16.49 | −3.08 | 43.60 |
| 4 | 19.11 | 21.36 | −7.36 | 54.19 |

As described above, the ΔE represents the degree of colour change. The results in Tables 2 and 3 therefore demonstrate that the dye treatment involving radio frequency radiation (Example 1) induced more colour change in the hair than where was instead provided with a straightening iron (Example 3), despite there being significantly lower induced temperatures in the case of the radio frequency radiation and the same treatment timescale.

Although results indicate that the strongest colour change was observed where the hair dye composition was left for 15 minutes without heating above ambient temperature (Example 2), satisfactory colour change was observed where radio frequency radiation was utilized (Example 1) at fraction of the time—150 mm of coated hair sample being completed within 30 seconds (5 mm/sec).

The invention claimed is:

1. A method of dyeing hair fibers, said method comprising the steps of:
    i) coating one or more hair fibers with a hair dye composition; and
    ii) directing radio frequency electromagnetic radiation having one or more frequencies from 1 MHz to 300 MHz to the one or more coated hair fibers to cause heating within the one or more coated hair fibers by dielectric loss.

2. The method according to claim 1, wherein the hair dye composition is a demi-permanent or permanent hair dye composition.

3. The method according to claim 1, wherein the hair dye composition is prepared by combining a dye lotion containing one or more dye precursors and an activator solution containing an activating agent, and the activating agent in the activator solution converts the one or more dye precursors in the dye lotion to active dye agents.

4. The method according to claim 3, wherein the activating agent is an oxidizing agent.

5. The method according to claim 1, wherein the hair fibers are keratinous fibers.

6. The method according to claim 1, wherein the hair fibers are human hair fibers.

7. The method according to claim 1, further comprising the preceding step of drying the one or more hair fibers prior to coating in step i).

8. The method according to claim 1, wherein after coating in step i) the one or more coated hair fibers are left for a period of time sufficient to allow impregnation of the hair dye composition into the one or more hair fibers before being subjected to radio frequency electromagnetic radiation in step ii).

9. The method according to claim 8, wherein said period of time is from 5 seconds to 500 seconds.

10. The method according to claim 1, wherein the one or more coated hair fibers are subjected to radio frequency electromagnetic radiation for a period of time which is from 0.5 to 30 seconds.

11. The method according to claim 1, wherein the temperature of the one or more coated hair fibers does not exceed 100° C. as a result of heating through dielectric losses in step ii).

12. The method according to claim 1, wherein
the radio frequency electromagnetic radiation has one or more frequencies of from 1 MHz to 100 MHz, and/or
the effective radiated power of the radio frequency electromagnetic radiation is from 10 W to 500 W.

13. The method according to claim 1, wherein the radio frequency electromagnetic radiation is provided by means of a device supplied with an alternating electrical current and comprising a radio frequency signal generator adapted for directing radio frequency electromagnetic radiation to hair fibers.

14. The method according to claim 13, wherein the radio frequency signal generator comprises plate electrodes in between which hair fibers are positioned to allow radio frequency electromagnetic radiation to be directed to the hair fibers.

15. The method according to claim 13, wherein
the device is a portable handheld appliance, and
the appliance comprises first and second opposing arms and the appliance is configured to generate radio frequency electromagnetic radiation in a region between the opposing arms such that hair fibers may be positioned in the region between the first and second opposing arms to allow radio frequency electromagnetic radiation to be directed to the hair fibers.

16. The method according to claim 15, wherein first and second opposing arms are movable between a closed position in which a contacting surface of the first arm is adjacent a contacting surface of the second arm and an open position in which the contacting surfaces of each arm are spaced apart.

17. The method according to claim 15, wherein directing radio frequency electromagnetic radiation to the coated hair fibers in step ii) comprises:
positioning the radio frequency signal generator of the appliance at one section of the one or more coated hair fibers; and
moving the appliance in the axial direction of the one or more coated hair fibers so as to direct radio frequency electromagnetic radiation over a length of the one or more coated hair fibers.

18. A kit comprising:
i) a hair dye composition;
ii) a handheld appliance for directing radio frequency electromagnetic radiation to one or more hair fibers; wherein the handheld appliance comprises a radio frequency signal generator adapted for directing radio frequency electromagnetic radiation to hair fibers when the appliance is supplied with an alternating electrical current, the handheld appliance being the handheld appliance defined in claim 15; and
one or both of:
a) instructions for use of the hair dye composition in coating one or more hair fibres and use of the handheld appliance for directing radio frequency electromagnetic radiation to the one or more coated hair fibers together as part of a hair dyeing process; and
b) an applicator for coating one or more hair fibers with a hair dye composition.

19. A handheld hair dyeing appliance comprising:
a radio frequency signal generator and first and second opposing arms,
wherein the appliance is configured to generate radio frequency electromagnetic radiation in a region between the opposing arms when the appliance is supplied with an alternating electrical current; and
wherein the appliance is adapted such that one or more hair fibers coated with a hair dye composition may be positioned in the region between the first and second opposing arms to allow radio frequency electromagnetic radiation to be directed to the coated hair fibers to cause heating within the one or more coated hair fibers by dielectric loss.

20. A method of dyeing a keratinous substrate, said method comprising the steps of:
i) coating a keratinous substrate with a dye composition; and
ii) directing radio frequency electromagnetic radiation having one or more frequencies from 1 MHz to 300 MHz to the coated keratinous substrate to cause heating within the keratinous substrate by dielectric loss, wherein the keratinous substrate includes skin and/or a nail.

* * * * *